(12) United States Patent
Varotto et al.

(10) Patent No.: US 8,952,249 B2
(45) Date of Patent: Feb. 10, 2015

(54) 1,4-FULLERENE ADDENDS IN PHOTOVOLTAIC CELLS

(75) Inventors: Alessandro Varotto, Santa Barbara, CA (US); Fred Wudl, Montecito, CA (US); Jang Jo, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 506 days.

(21) Appl. No.: 13/161,827

(22) Filed: Jun. 16, 2011

(65) Prior Publication Data

US 2011/0313189 A1  Dec. 22, 2011

Related U.S. Application Data

(60) Provisional application No. 61/397,947, filed on Jun. 18, 2010.

(51) Int. Cl.
| | | |
|---|---|---|
| C07C 69/616 | (2006.01) |
| C07C 25/22 | (2006.01) |
| C07C 211/61 | (2006.01) |
| C07C 43/21 | (2006.01) |
| C07C 39/42 | (2006.01) |
| B82Y 10/00 | (2011.01) |
| B82Y 20/00 | (2011.01) |
| B82Y 30/00 | (2011.01) |
| H01L 51/00 | (2006.01) |
| H01L 51/42 | (2006.01) |

(52) U.S. Cl.
CPC ............... *C07C 25/22* (2013.01); *B82Y 10/00* (2013.01); *B82Y 20/00* (2013.01); *B82Y 30/00* (2013.01); *C07C 43/21* (2013.01); *C07C 69/616* (2013.01); *C07C 211/61* (2013.01); *H01L 51/0047* (2013.01); *C07C 2104/00* (2013.01); *H01L 51/0036* (2013.01); *H01L 51/0037* (2013.01); *H01L 51/0043* (2013.01); *H01L 51/4226* (2013.01); *H01L 51/4253* (2013.01); *Y02E 10/549* (2013.01); *Y10S 977/738* (2013.01)
USPC ........... 136/263; 136/252; 560/102; 568/632; 568/633; 568/732; 570/129; 564/308; 977/738

(58) Field of Classification Search
USPC ........... 136/263; 568/632, 633, 732; 564/308; 570/129; 977/778
See application file for complete search history.

(56) References Cited

U.S. PATENT DOCUMENTS

| | | | | |
|---|---|---|---|---|
| 2007/0062577 A1* | 3/2007 | Koppe | .......................... | 136/263 |
| 2009/0266416 A1* | 10/2009 | Tolbert et al. | ................. | 136/256 |
| 2011/0005597 A1* | 1/2011 | Sato et al. | ..................... | 136/263 |

FOREIGN PATENT DOCUMENTS

WO    WO 2009008323 A1 *  1/2009

OTHER PUBLICATIONS

Hoppe et al., "Polymer Solar Cells" from "Advances in polymer science", 2008.*
"1,4 Fullerene Derivatives: Tuning the Properties of the Electron Transporting Layer in Bulk heterojunction Solar Cells".).*

(Continued)

*Primary Examiner* — Matthew Martin
(74) *Attorney, Agent, or Firm* — Gates & Cooper LLP

(57) ABSTRACT

1,4 fullerene deriatives useful for solar cells are provided, where their structures allow for straightforward functionalizations to tune their properties in terms of solubility and LUMO energy levels.

19 Claims, 5 Drawing Sheets

(56) References Cited

OTHER PUBLICATIONS

Barry, C. T.; Jean, M. J. F., Polymer-Fullerene Composite Solar Cells. Angew. Chem. Int. Ed. 2008, 47; (1), 58-77.

Hummelen, J. C.; Knight, B. W.; LePeq, F.; Wudl, F.; Yao, J.; Wilkins; C. L., Preparation and Characterization of Fulleroid and Methanofullerene Derivatives. J. Org. Chem. 1995, 60, (3), 532-538.

Lacramioara M. Popescu; Patrick van 't Hof; Alexander B. Sieval; Harry T. Jonkman; Hummelen, J. C., Thienyl analog of 1-(3-methoxycarbonyl)propyl-1-phenyl-[6,6]-methanofullerene for bulk heterojunction photovoltaic devices in combination with polythiophenes. Appl. Phys. Lett. 2006, 89, 213507.

Changduk, Y.; Shinuk, C.; Alan , J. H.; Fred, W., Heteroanalogues of PCBM: N-Bridged Imino-PCBMs for Organic Field-Effect Transistors. Angew. Chem. Int. Ed. 2009, 48, (9), 1592-1595.

Backer, S. A.; Sivula, K.; Kavulak, D. F.; Frechet, J. M. J., High Efficiency Organic Photovoltaics Incorporating a New Family of Soluble Fullerene Derivatives. Chem. Mater. 2007, 19, (12), 2927-2929.

Wang, G,-W.; Lu, Y.-M.; Chen, Z.-X., 1,4-Fullerenols C60ArOH: Synthesis and Functionalization. Org. Lett. 2009, 11, (7), 1507-1510.

Matsuo, Y.; Sato, Y.; Niinomi, T.; Soga, I.; Tanaka, H.; Nakamura, E., Columnar Structure in Bulk Heterojunction in Solution-Processable Three-Layered p-i-n Organic Photovoltaic Devices Using Tetrabenzoporphyrin Precursor and Silylmethyl[60]fullerene. J. Am. Chem. Soc. 2009, 131, (44), 16048-16050.

Illescas, B. M.; Martin, N., [60]Fullerene-based electron acceptors. Comptes Rendus Chimie 2006, 9, (7-8); 1038-1050.

Kooistra, F. B.; Knol, J.; Kastenberg, F.; Popescu, L. M.; Verhees. W. J. H.; Kroon, J. M.; Hummelen, J. C., Increasing the Open Circuit Voltage of Bulk-Heterojunction Solar Cells by Raising the LUMO Level of the Acceptor. Org. Lett. 2007, 9, (4), 551-554.

Brebec, C. J.; Crevino, A.; Meissner, D.; Sariciftci, N. S.; Frornherz, T.; Rispens; M. T.; Sanchez, L.; Hummelen, J. C., Origin of the Open Circuit Voltage of Plastic Solar Cells. Adv. Funct. Mater. 2001, 11, (5), 374-380.

\* cited by examiner

PCVM

PTHOB

PFOH

PFTFP

ANP

1,4-FULLERENE ADDENDS IN PHOTOVOLTAIC CELLS

CROSS REFERENCE TO RELATED APPLICATION

This application claims the benefit of U.S. provisional patent application Ser. No. 61/397,947 which was filed on Jun. 18, 2010, which is hereby incorporated by reference in its entirety.

FIELD OF THE INVENTION

The invention relates to fullerene polymers compositions for photovoltaic cells. More particularly, the use of 1,4 fullerene addends for photovoltaic cells, and fine tuning of their solubility and LUMO levels.

BACKGROUND OF THE INVENTION

Chemically modified fullerene derivatives are of great interest as electron acceptors in organic photovoltaics.[1] The vast majority of derivatives synthesized and employed so far are based on the 1,2 addition on a 6 member ring. The 1,2 addends class include [6,6]-phenyl-$C_{61}$-butyric acid methyl ester (PCBM)[2] and thio-PCBM,[3] which are commercial products, its azoanalogues[4] and a variety of other derivatives bearing different functional groups.[1] Previous reports on fullerene derivatives employed in solar cells demonstrated that small and subtle modifications of the appended functionalities can lead to dramatic and often unpredictable changes in the performance of the device.[1] Nevertheless, most of the attempted studies, with few exceptions,[5] brought to a decreased efficiency when compared to that one of PCBM.

BRIEF SUMMARY OF THE INVENTION

'Fullerenes', as used hereafter, is a generic term to represent fullerenes C60, C70, C84 and higher fullerenes. Accordingly, although the working examples show fullerene C60 derivatives, the invention is also applicable to fullerenes C70, C84 and higher fullerene derivatives. Moreover, although the various figures and structures show only fullerene C60 derivatives, it is to be understood that the structure also represents fullerene C70, C84 or higher fullerene derivatives.

Novel 1,4 fullerene derivatives are provided that are less symmetrical than those previous reported and therefore they absorb more light. Their new chemistry allows for straightforward functionalization to tune their properties.

In one embodiment, a photovoltaic cell is provided comprising a 1,4 fullerene derivative selected from a group consisting of:

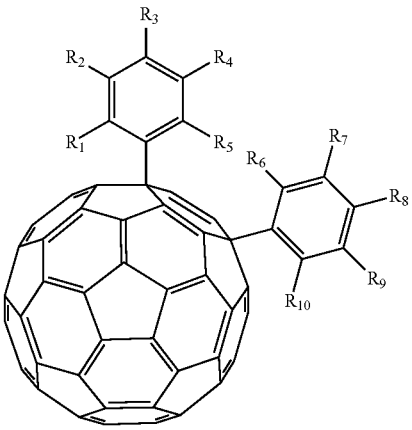

Structure I and

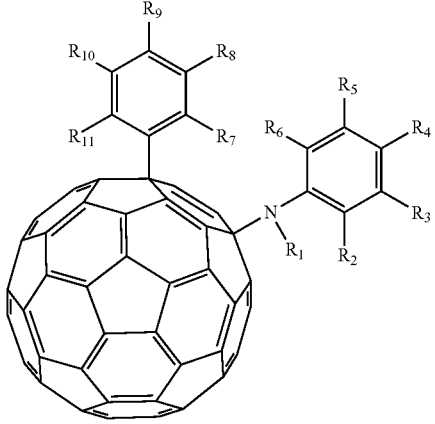

Structure II wherein the fullerene can either be fullerene C60, C70, C84 or higher;

wherein for structure I, R1-R10 can each independently be selected from hydrogen, alkyl, aryl, amino, oxo, thio, alkyl, halogen, and silanes;

and wherein for structure II, R1 can be hydrogen or alkyl group, and R2-R11 can each independently be selected from hydrogen, alkyl, aryl, amino, oxo, thio, alkyl, halogen, and silanes.

In a more particular embodiment, the 1,4 fullerene derivative is selected from a group consisting PEHOB; PCVM; PTHOB; PFTFP, and ANP.

In yet another embodiment, a method for tuning the solubility of a compound for a photovoltaic cell is provided comprising arylating a fullerenol with a long alkyl chain group to produce a compound, and determining whether said compound is soluble in a solvent.

In another embodiment, a method for fine tuning the LUMO level of a fullerene derivative for a photovoltaic cell is provided comprising arylating a fullerenol with an electron withdrawing group to lower the LUMO level of the derivative, or an electron donating group to raise the LUMO level of the derivative.

In yet another embodiment, a method of producing a photovoltaic cell device is provided comprising forming a layer of the device with a compound comprising a 1,4 fullerene derivative.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

We herein introduce a new class of fullerene derivatives based on the 1,4 addition chemistry.[6]

The interest for the synthesis of 1,4 addends include: (i) lower symmetry with consequent increased optical absorption in the visible (onset at ca. 500 nm and extinction coefficient of ca. 8000 $mol^{-1}$ $cm^{-1}$); (ii) new chemistry which allows for straightforward functionalization and (iii) possibility to tune solubility and energy of the LUMO. The enhanced absorption can favorably affect the short circuit current ($J_{sc}$) by increasing the number of photo-charges generated in the electron-transporting layer of the device. Tuning the energy of the LUMO is desirable to couple the fullerene with a specific donor polymer. Data obtained from devices incorporating these addends is encouraging. To the best of our knowledge, only one 1,4-fullerene addend was used in solution processed solar cells and it was based on a benzoporphyrin and not a polymer.[7] These derivatives can be tuned for their solubility by assessing whether they are soluble in solvents, such as but not limited to, chlorobenzene, 1,2-dichlorobenzene or chloroform.

A 1,4 fullerene derivative with the following structure is provided:

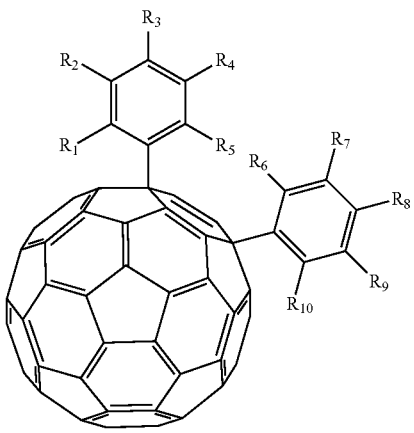

wherein the fullerene can either be fullerene C60, C70, C84 or higher;

where R1-R10 can each independently be selected from hydrogen, alkyl, aryl, amino, oxo, thio, alkyl, halogen, and silanes.

In another embodiment, R1-R10 can be long alkyl chains such as, but not limited to 2-ethylhexyloxy, and valeric acid methyl ester.

In yet another embodiment, R1-R10 can be electron withdrawing groups to stabilize/lower the energy of the LUMO of the derivative, such as but not limited to, halogens (F, Cl), nitriles, carbonyls, and nitro groups.

In another embodiment, R1-R10 can be electron donating groups to destabilize/raise the energy of the LUMO of the derivative, such as but not limited to, alkyl, alkyloxy, alcohol, amino, and silanes.

In yet another embodiment, the following 1.4 fullerene derivative is provided:

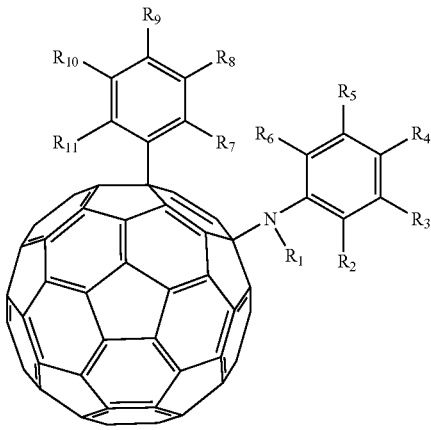

wherein the fullerene can either be fullerene C60, C70, C84 or higher;

where R1 can be hydrogen or alkyl group, and R2-R11 can each independently be selected from hydrogen, alkyl, aryl, amino, oxo, thio, alkyl, halogen, and silanes.

Results and Discussion

Figure 1:
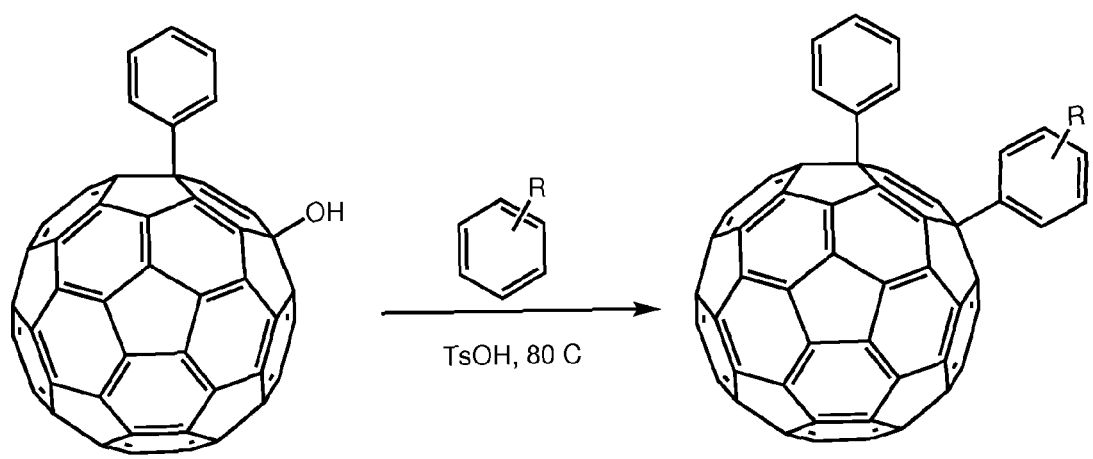
FIG. 1 shows a scheme for the synthesis of a set of fullerene derivatives by arylation.

The synthesis of fullerenol was previously reported.[6] From fullerenol, we herein report on the syntheses of a set of derivatives by arylation as described in FIG. 1. In a typical reaction, fullerenol is reacted with a specific substrate (a substituted aryl) used as the solvent in the presence of p-toluene sulfonic acid (TsOH) as the catalyst. Following this procedure we synthesized: PEHOB (FIG. 2) ($C_{60}$ functionalized with a phenyl group on C1 and an ethylhexyloxybenzene group on C4), PCVM (FIG. 3) (Phenyl on C1 and phenylvaleric acid methyl ester on C4), PTHOB (FIG. 4) (phenyl on C1 and trihexyloxyphenyl on C4), PFOH (FIG. 5) (phenyl on C1 and hydroxyl on C4); PFTFP (FIG. 6) (p-trifluorophenyl on C1 and pentafluorophenyl on C4) and ANP (FIG. 7) (phenyl on C1 and aniline on C4). 1H NMR, 13C NMR, 19F NMR and field desorption (FD) mass spectroscopy confirmed the identity of the products. The adducts were further characterized by cyclic voltammetry (CV) and UV-vis spectroscopy. All the fullerene derivatives displayed a nearly identical UV-vis profile with a broad signal at ca. 470 nm, typical for lower symmetrical derivative (see FIG. 8). The lower symmetry was also confirmed by 13C NMR, which showed at least 40 signals for the $sp^2$ fullerene carbons; this is consistent with a $C_1$ symmetry. From the first reduction potential calculated by CV we determined the energy of the LUMO. An estimated value of the HOMO was inferred from the onset of the UV-vis spectra. In order to modify the property of the derivatives, we appended (i) long alkyl chains to increase solubility and (ii) electron withdrawing or (iii) electron donating groups to stabilize or destabilize the energy of the LUMO respectively. Due to the spherical shape of $C_{60}$, heteroatoms or functional groups appended on the fullerene can only affect the energy of the molecular orbitals by induction. Therefore, an electron donating group directly bound to $C_{60}$ such a methoxy will stabilize the energy of the LUMO because of the higher electronegativity of the oxygen. Nevertheless, alkyloxy groups bound to a phenyl bound to $C_{60}$, can exert their properties as electron donating groups either by resonance into the phenyl or through space.[8] We started from the synthesis of the simplest derivatives bearing 2 phenyl groups on C1 and C4 (procedure described in the literature)[6]. The energy of the LUMO for this derivative was −3.75 eV (same as PCBM). By changing the nature and the number of heteroatoms on the phenyl on C4 we lowered the LUMO of ca. 200 mV and rose it of ca. 100 mV. These values are in agreement with previous reports.[8, 9] Table 1 (see below) summarizes the electrochemical data calculated for all the derivatives. The interest for tuning the LUMO is to increase the number of possible combinations with novel low band-gap polymers. Also, the difference in energy between the HOMO of the donor and the LUMO of the acceptor is reported to determine the open circuit voltage ($V_{oc}$) of the device.[10] Thus, to increase the LUMO can lead to an increased $V_{oc}$. Compared to the PCBM analogues described by Hummelen[9] et al., the 1,4-fullerene addends with sub-stituents directly appended appear to affect their redox potentials to a greater degree. For instance, one pentafluoro-phenyl group on PCBM raises the redox potential from −1.08 mV (PCBM) to −1.042 mV (net change 0.038 V), whereas PFTFP is increased from −1.02 to −0.910 mV (net change 0.11 V)

Figure 9:
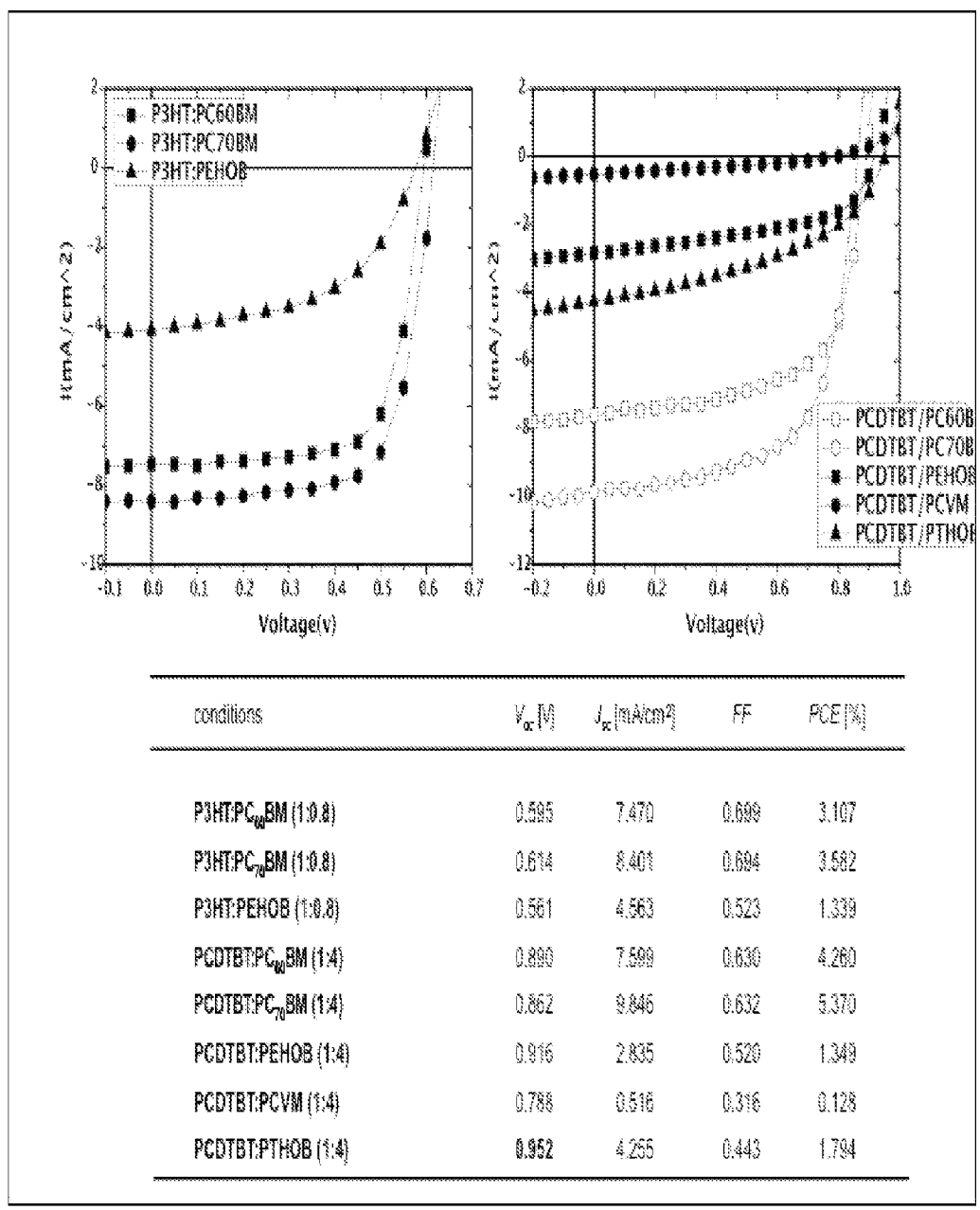
FIG. 9 shows I-V curves and OPV parameters of some devices.

Device data of bulk heterojunction (BHJ) solar cells fabricated with PEHOB/P3HT show that the efficiency is of the same order of magnitude of that one of PCBM. The solar cells fabricated with PEHOB and PTHOB derivatives displayed very high $V_{oc}$, in particular PTHOB had a $V_{oc}$ higher than $PC_{70}BM$ (FIG. 9).

Conclusions

In summary we have synthesized a set of 1,4-fullerene addends and varied the properties of the materials by tuning the solubility and the energy of the LUMO. By introduction of electron withdrawing groups we increased the electron accepting properties. By introducing electron donating groups, we decreased the electron acceptor properties with the possibility to increase the Voc of the device.

EXPERIMENTAL DETAILS

FIG. 1 is a scheme showing arylation of fullerenol. R═H, —$CH_3$, —$OCH_3$, —Fs, 2-ethylhexyloxybenzene, phenylvaleric acid methyl ester, —NH.

Synthesis of PEHOB

Figure 2:
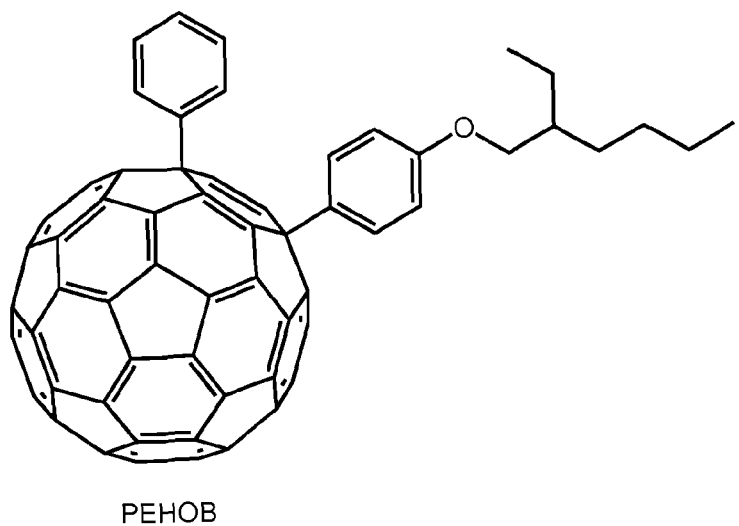
FIG. 2 shows the structure of PEHOB.

FIG. 2 shows the structure of PEHOB.

To a solution containing fullerenol (300.0 mg, 0.37 mol) in 6 mL of 2-ethylhexyloxybenzene, TsOH (350 mg, 1.84 mol) was added. The mixture was heated and stirred in an oil bath preset at 80 C. The reaction was monitored by TLC and stopped after 12 hours. After cooling, the mixture was poured in a centrifuge tube and the products precipitated with 15 mL of methanol. After removing the supernatant, the precipitate was chromatograph on silica gel (6×25 cm) using $CS_2$ as eluent. The first fraction afforded ca. 5 mg of a brown compound that was not characterize. A second fraction was eluted (ca. 1 mg). The third fraction ($R_f$=0.72) afforded PEHOB (35 mg, 10%). The solution was concentrated to ca. 5 mL under reduced pressure and precipitated with 15 mL of methanol. After centrifuging and removing the supernatant, this procedure was repeated 3 more times. Using $CS_2$/Toluene (2/1, v/v) we recovered 65% of fullerenol.

$^1$H NMR (500 MHz, $CS_2/CDCl_3$) δ ppm 1.6-0.9 (m, 12H), 1.78 (m, 1H), 3.9 (d, 2H), 7.01 (d, 2H), 7.47 (m, 1H), 7.55 (m, 2H), 7.97 (d, 2H), 8.13 (d, 2H). 13C NMR (500 MHz, $CS_2$/DMSO-d6 1/1 v/v) δ ppm 11.40, 14.39, 23.46, 24.19, 29.26, 29.91, 30.68, 61.50 ($sp^3$-C of $C_{60}$), 61.95 ($sp^3$-C of $C_{60}$), 70.14 ($OCH_2$), 115.09 (aryl C), 127.31 (aryl C), 128.16 (aryl C), 128.34 (aryl C), 129.27 (aryl C), 131.62 (aryl C), 136.96, 137.19, 138.48, 138.60, 139.95, 140.71, 141.80, 142.01, 142.31, 142.35, 142.47, 142.84, 142.90, 142.93, 143.58, 143.67, 143.74, 143.93, 143.99, 144.03, 144.09, 144.49, 144.63, 144.76, 144.82, 145.20, 145.27, 146.54, 146.63, 146.70, 146.83, 148.15, 148.27, 148.34, 150.58, 151.03, 156.36, 156.64, 159.01. $FD^+$ 1002.2. UV-vis (1,2-dichlorobenzene) $\lambda_{max}$/nm 334, 446, 540, 620, 690.

Synthesis of PCVM

Figure 3:
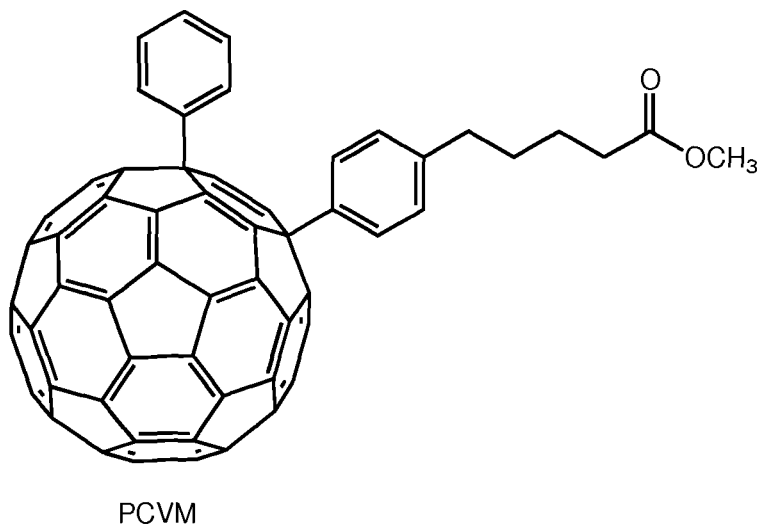
FIG. 3 shows the structure of PCVM.

FIG. 3 shows the structure of PCVM.

Phenylvaleric acid (7 g) was melted and heated at 80 C in a 25 mL round bottomed flask. Fullerenol (225 mg, 0.28 mmol) and TsOH (260 mg, 1.38 mmol) were added and the solution was stirred for 12 hours. The solution was cooled down to room temperature and methanol (15 mL) was added. After centrifugation, the supernatant was removed and this procedure repeated 2 more times. The crude was not characterized but was further reacted to produce the methyl ester according to the following procedure: 260 mg of crude was dissolved in 6 mL of 1,2-dichlorobenzene and stirred. Methanol (1.5 mL) and concentrated HCl (0.2 mL) were added and the mixture was stirred and heated at 45 C for 12 hours. The mixture was cooled to room temperature and poured into 15 mL of methanol, centrifuged and washed again with methanol for 3 times according to the general procedure described earlier. The crude was chromatographed on silica gel (6×20 cm). Using $CS_2$ as the eluent a first fraction, which was not characterized, was eluted. The second fraction ($R_f$=0.62) was collected and afforded of a fullerene derivative bearing a phenyl on C1 and —OCH₃ group on C4 (45 mg). Using CS₂/Toluene 2/1 v/v we recovered fullerenol (third fraction) and PCVM (35 mg, fourth fraction).

¹H NMR (500 MHz, CS₂/CDCl₃ 2/1) δ ppm 1.74-1.76 (m, 4H), 2.39 (t, 2H), 2.76 (t, 2H), 3.69 (s, 3H), 7.31 (d, 2H), 7.47 (m, 1H), 7.53 (m, 2H), 7.95 (d, 2H), 8.01 (d, 2H). 13C NMR (500 MHz, CS₂/CDCl₃ 2/1 v/v) δ ppm 24.85, 31.12, 34.04, 35.62, 51.38 (OCH₃), 61.64 (sp³-C of C₆₀), 61.83 (sp³-C of C₆₀), 70.14 (OCH₂), 127.69 (aryl C), 127.72 (aryl C), 128.41 (aryl C), 129.52 (aryl C), 137.57, 137.61, 138.14, 138.98, 139.05, 140.62, 141.20, 142.25, 142.28, 142.41, 142.72, 142.80, 142.91, 143.33, 143.37, 144.01, 144.05, 144.11, 144.16, 144.39, 144.46, 144.52, 144.91, 145.03, 145.12, 145.25, 145.50, 145.72, 147.01, 147.11, 147.16, 147.29, 148.61, 148.67, 148.83, 151.02, 151.25, 156.77, 156.86, 173.40. UV-vis (1,2-dichlorobenzene) $\lambda_{max}$/nm 334, 446, 540, 620, 690.

Synthesis of PTHOB

Figure 4:
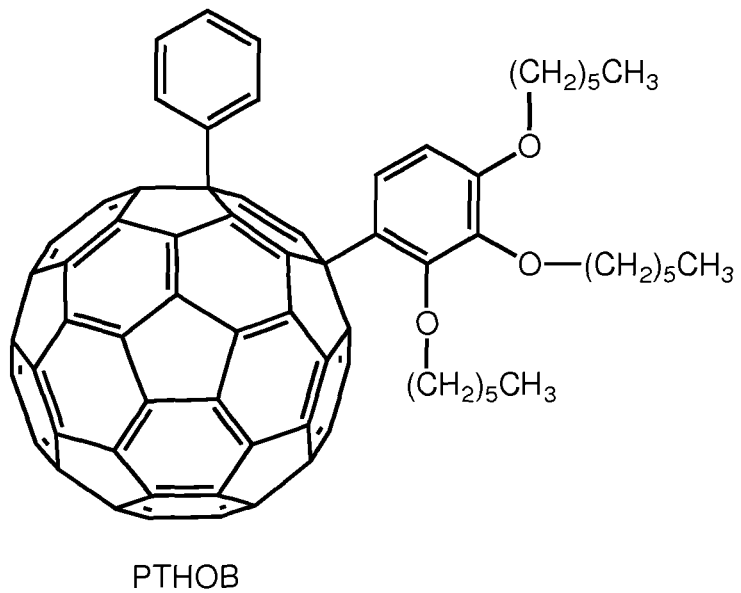
FIG. 4 shows the structure of PTHOB.

FIG. 4 shows the structure of PTHOB.

To a solution containing fullerenol (460.0 mg, 0.57 mol) in 7 mL of trihexyloxybenzene (synthesized according to literature procedure), TsOH (537 mg, 2.28 mol) was added. The mixture was heated and stirred in an oil bath preset at 80 C. The reaction was monitored by TLC and stopped after 12 hours. The mixture was poured in a centrifuge tube and the products precipitated with 15 mL of methanol. After removing the supernatant, the precipitate was chromatograph on silica gel (6×25 cm) using CS₂ as eluent. The first fraction afforded ca. 10 mg of a brown compound that was not characterize. A second fraction was eluted (ca. 1 mg). The third fraction ($R_f$=0.72) afforded PTHOB (120 mg, 19%). The fraction was concentrated to ca. 5 mL under reduced pressure and precipitated with 15 mL of methanol. After centrifuging and removing the supernatant, this procedure was repeated 3 more times. Using CS₂/Toluene 2/1 v/v we recovered 35% of fullerenol.

¹H NMR (500 MHz, CDCl₃) δ ppm 0.94 (m, 10H), 1.39 (m, 14H), 1.70 (m, 2H), 1.8 (s, 4H), 4.08 (m, 4H), 4.25 (m, 2H), 6.78 (d, 1H), 7.43 (m, 1H), 7.47 (m, 2H), 7.81 (d, 1H), 8.09 (d, 2H). 13C NMR (600 MHz, CDCl3) δ ppm 14.03, 14.10, 22.58, 22.58, 22.67, 22.71, 25.60, 25.88, 29.39, 29.91, 31.67, 31.72, 31.85, 59.61, 61.72, 68.90, 73.80 (sp³-C of C₆₀), 74.36 (sp³-C of C₆₀), 108.21, 124.20, 126.52, 127.70, 128.03, 129.26, 137.96, 137.99, 138.80, 138.96, 140.89, 141.82, 142.20, 142.30, 142.45, 142.67, 142.82, 142.86, 143.06, 143.21, 143.26, 143.28, 143.43, 143.63, 143.84, 143.92, 144.03, 144.10, 144.24, 144.39, 144.42, 144.46, 144.49, 144.56, 144.65, 144.67, 144.91, 145.02, 145.05, 145.22, 145.26, 145.57, 145.61, 145.67, 145.90, 146.87, 146.92, 147.14, 147.20, 147.48, 147.62, 148.20, 148.73, 148.89, 150.79, 151.57, 152.53, 153.91, 156.33, 156.98, UV-vis (1,2-dichlorobenzene) $\lambda_{max}$/nm 334, 446, 540, 620, 690.

Synthesis of PFOH

Figure 5:
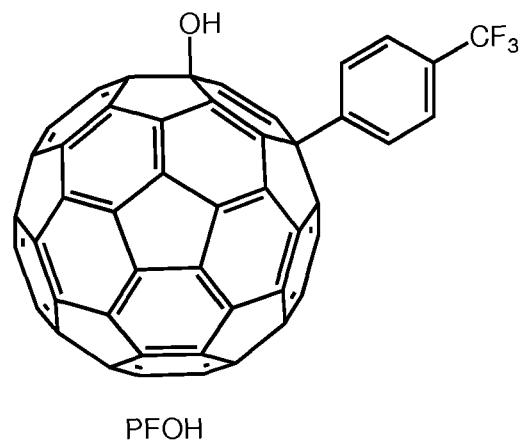
FIG. 5 shows the structure of PFOH.

FIG. 5 shows the structure of PFOH.

Fullerene C₆₀ (1 g, 1.39 mol), p-trifluoromethylphenylhydrazine (490 mg, 2.78 mol) and NaNO2 (192 g, 2.78 mol) were sonicated in toluene (750 mL) for 10 minutes. Concentrated HCl (0.2 mL) and water (30 mL) were added and the mixture was stirred in an oil bath preset at 50 C for 6 hours. The solvent was removed under reduced pressure and the crude was chromatographed on silica gel (6×15 cm). Unreacted C₆₀ (50%) was recovered using CS₂ as the eluent. Trifluoromethylfullerenol (PFOH) was recovered using CS₂/Toluene 2/1 v/v (200 mg, 16% yield).

¹H NMR (500 MHz, CS₂/CDCl₃) δ 4.06 (s, 1H), 7.93 (d, 2H), 7.53 (d, 2H). 19F NMR (500 MHz, CS₂/CDCl₃) δ 62.13 (s). 13-C NMR (500 MHz, CS₂/CDCl₃) δ 61.03 (sp³-C of C₆₀), 75.64 (sp³-C of C₆₀), 126.70, 126.73, 137.83, 138.80, 139.09, 139.76, 141.34, 141.50, 141.60, 142.25, 142.48, 142.55, 142.70, 142.80, 143.14, 143.21, 143.37, 143.40, 143.49, 143.53, 143.63, 143.73, 143.86, 143.97, 144.02, 144.15, 144.20, 144.24, 144.32, 144.39, 144.60, 144.76, 144.6, 145.37, 145.79, 145.83, 145.97, 146.75, 146.90, 147.11, 147.17, 147.21, 147.27, 147.34, 147.98, 148.72, 149.14, 150.43, 151.27, 152.71, 152.97. FD⁺ 882.0. UV-vis (1,2-dichlorobenzene) $\lambda_{max}$/nm 334, 446, 540, 620, 690.

Synthesis of PFTFP

Figure 6:
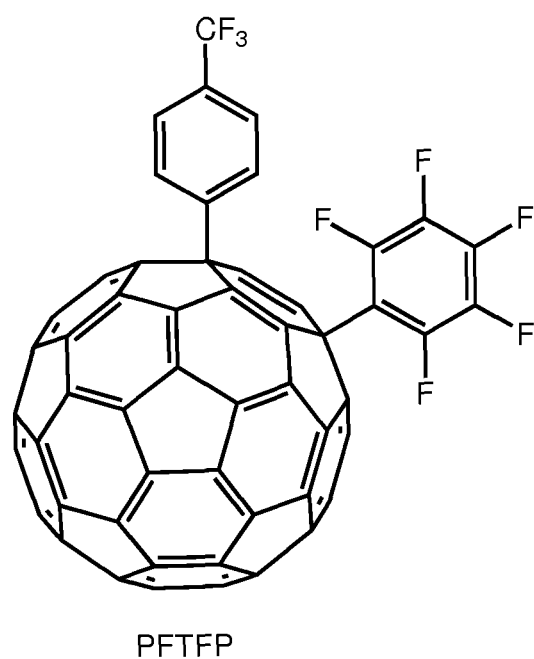
FIG. 6 shows the structure of PFTFP.

FIG. 6 shows the structure of PFTFP.

PFOH (50.0 mg, 0.06 mol) was stirred in 7 mL of either hexafluorobenzene or pentafluorobenzene. TsOH (54 mg, 0.28 mol) was added. The mixture was heated and stirred in an oil bath preset at 70 C. The reaction was monitored by TLC and stopped after 12 hours. The solvent was removed under reduced pressure. The residue was chromatograph on silica gel (6×10 cm) using CS₂ as eluent. The first fraction afforded 25 mg of PFTFP (40% yield). The product was not soluble enough to obtain a clear NMR spectrum. Nevertheless mass spectroscopy confirmed the identity of the compound and 19F NMR revealed the presence of several fluorines. We speculate that some of the fluorines might undergo fluorodeprotonation and that the product might be a mixture of isomers with partially non-fluorinated phenyl. FD⁺K 1070.1. UV-vis (1,2-dichlorobenzene) $\lambda_{max}$/nm 334, 446, 540, 620, 690.

Synthesis of ANP

Figure 7:
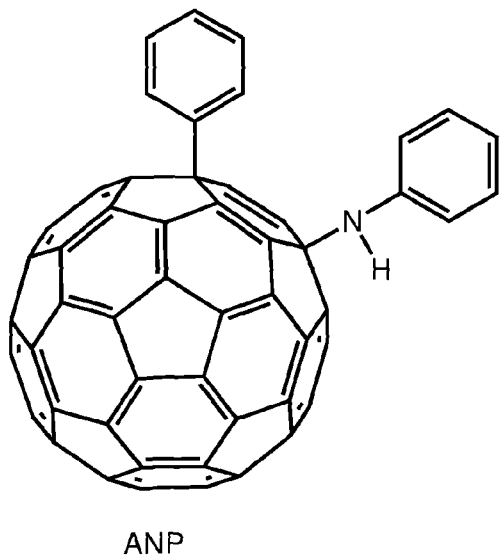
FIG. 7 shows the structure of ANP.

FIG. 7 shows the structure of ANP.

Fullerenol (130.0 mg, 0.16 mol) was stirred in 7 mL of aniline TsOH (175 mg, 0.92 mol) was added. The mixture was heated and stirred in an oil bath preset at 80 C. The reaction was monitored by TLC and stopped after 12 hours. The mixture was poured in a centrifuge tube and the products precipitated with 15 mL of methanol. After removing the supernatant, the precipitate was chromatograph on silica gel (6×15 cm) using CS₂ as eluent. The first fraction afforded 55 mg of ANP (39% yield).

¹H NMR (500 MHz, CS₂/CDCl₃) δ 5.34 (s, 1H), 7.02 (m, 1H), 7.32 (m, 2H), 7.52 (m, 3H), 7.65 (m, 2H), 8.37 (d, 2H). 13-C NMR (500 MHz, CS₂/CDCl₃) δ 61.87 (sp³-C of C₆₀), 67.35 (sp³-C of C₆₀), 120.69 (aryl C), 122.45 (aryl C), 127.86 (aryl C), 128.50 (aryl C), 129.53 (aryl C), 129.77 (aryl C), 138.07, 138.12, 139.38, 139.61, 140.61, 141.05, 141.48, 142.17, 142.46, 142.63, 142.71, 142.75, 143.03, 143.10, 143.28, 143.39, 143.46, 143.57, 143.72, 143.79, 143.97, 144.24, 144.28, 144.33, 144.38, 144.61, 144.68, 144.83, 144.95, 145.24, 145.57, 145.57, 145.75, 145.89, 146.61, 146.80, 146.95, 147.14, 147.20, 147.29, 147.32, 147.72, 147.89, 148.68, 148.83, 148.98, 149.79, 152.60, 152.70, 155.03. UV-vis (1,2-dichlorobenzene) $\lambda_{max}$/nm 334, 446, 540, 620, 690.

Fabrication of the Devices

1. The solar cell devices were fabricated on indium tin oxide (ITO)-coated glass substrates, which were previously cleaned by ultrasonication with detergent, deionized water, acetone, and isopropyl alcohol, sequentially. Poly(3,4-ethylenedioxythiophene):poly(styrenesulfonate) (PEDOT:PSS) (Baytron PH) was spin-coated onto the ITO-coated glass and then baked at 140° C. for 10 min in air.

2a. PCDTBT-based cells: After transferring to a N₂-filled glove box, the blend solution (0.7 wt %) PCDTBT:acceptor (1:4 ratio by weight), which was dissolved in cosolvent of 1,2-dichlorobenzene (DCB) and chlorobenzene (CB) (3:1 ratio by volume), was spin-cast (6000 rpm, 40 s) onto the PEDOT:PSS layer. The film was dried for 10 min at 70° C. in the glove box.

2b. P3HT-based cells: The P3HT:acceptor weight ratio was fixed at 1:0.8. P3HT and acceptor (1 wt %) were dissolved in DCB in a N2-filled glove box. The active layers of each device were formed by spin-coating (800 rpm, 60 s), with the blend solutions passing through a 0.2 mm PTFE filter on the PEDOT:PSS layer. For the devices fabricated by the solvent-annealing process, the growth rate of the blend films was controlled by keeping the spin-coated films in a small, capped glass jar to protect against fast solvent evaporation and penetration of outside N2 gas during 30 min. The film was annealed for 10 min at 110° C. in the glove box.

3. The TiOx precursor solution diluted 1:200 in methanol was spin-coated in air on top of the PCDTBT:PC70BM layer (5,000 rpm, 40 s). The sample was heated at 80° C. for 10 min in air. To complete the device fabrication, an Al electrode (100 nm) was deposited on top of the photoactive layer by thermal evaporation under high vacuum ($<3\times10^{-6}$ torr).

Figure 8:
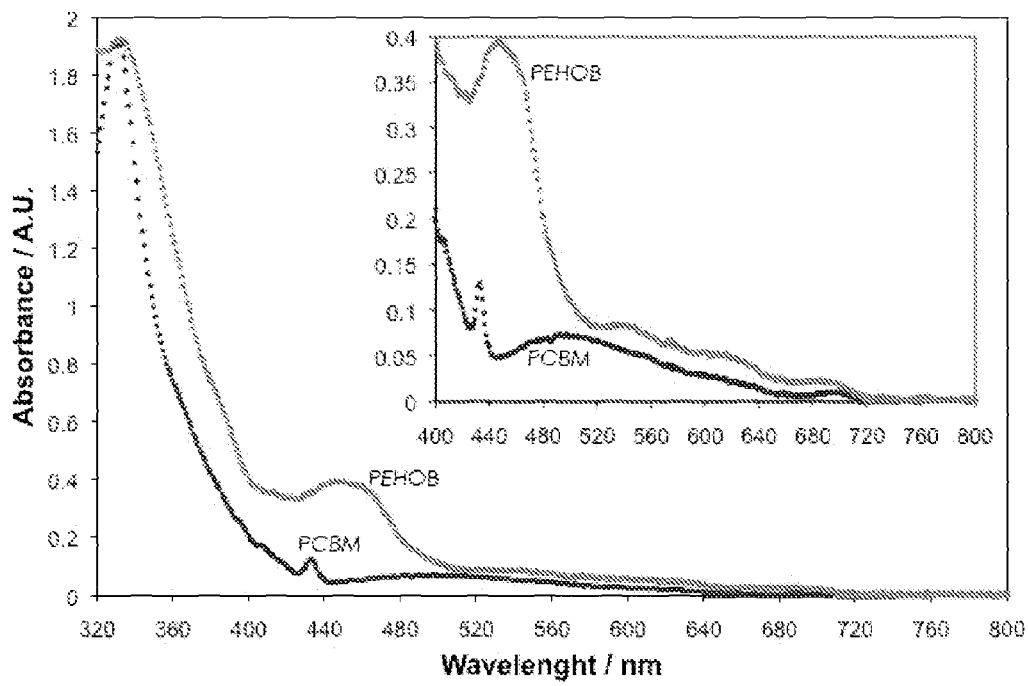
FIG. 8 shows absorbance/wavelength spectra graph of PEHOB and PCBM in 1,2-dichlorobenzene.

FIG. 8 shows a UV-vis of PEHOB (pink) and PCBM (blue) in 1,2-dichlorobenzene.

| Derivative | LUMO (eV) | $E^1_{red}$ | $E^2_{red}$ | $E^3_{red}$ |
|---|---|---|---|---|
| PCBM | −3.74 | −1.056 | −1.471 | −1.957 |
| PEHOB | −3.74 | −1.062 | −1.496 | −1.963 |
| PCVM | −3.76 | −1.021 | −1.484 | −1.959 |
| PFOH | −3.86 | −0.940 | −1.460 | −1.894 |
| PFTFP | −3.91 | −0.911 | −1.375 | |
| PTHOB | −3.65 | −1.150 | −1.589 | −2.072 |
| ANP | −3.81 | −0.992 | −1.532 | −1.900 |

Table 1 shows electrochemical data and energy of the LUMO. Experimental conditions: values in V vs Fc/Fc$^+$; 1,2-dichlorobenzene, Bu4NClO4 (0.1 M) as supporting electrolyte. Pt wire counter electrode; 50 mV/s scan rate.

FIG. 9 shows I-V curves and OPV parameters of some devices.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

REFERENCES

1. Barry, C. T.; Jean, M. J. F., Polymer-Fullerene Composite Solar Cells. *Angew. Chem. Int. Ed.* 2008, 47, (1), 58-77.
2. Hummelen, J. C.; Knight, B. W.; LePeq, F.; Wudl, F.; Yao, J.; Wilkins, C. L., Preparation and Characterization of Fulleroid and Methanofullerene Derivatives. *J. Org. Chem.* 1995, 60, (3), 532-538.
3. Lacramioara M. Popescu; Patrick van 't Hof; Alexander B. Sieval; Harry T. Jonkman; Hummelen, J. C., Thienyl analog of 1-(3-methoxycarbonyl)propyl-1-phenyl-[6,6]-methanofullerene for bulk heterojunction photovoltaic devices in combination with polythiophenes. *Appl. Phys. Lett.* 2006, 89, 213507.
4. Changduk, Y.; Shinuk, C.; Alan, J. H.; Fred, W., Heteroanalogues of PCBM: N-Bridged Imino-PCBMs for Organic Field-Effect Transistors. *Angew. Chem. Int. Ed.* 2009, 48, (9), 1592-1595.
5. Backer, S. A.; Sivula, K.; Kavulak, D. F.; Frechet, J. M. J., High Efficiency Organic Photovoltaics Incorporating a New Family of Soluble Fullerene Derivatives. *Chem. Mater.* 2007, 19, (12), 2927-2929.
6. Wang, G.-W.; Lu, Y.-M.; Chen, Z.-X., 1,4-Fullerenols C60ArOH: Synthesis and Functionalization. *Org. Lett.* 2009, 11, (7), 1507-1510.
7. Matsuo, Y.; Sato, Y.; Niinomi, T.; Soga, I.; Tanaka, H.; Nakamura, E., Columnar Structure in Bulk Heterojunction in Solution-Processable Three-Layered p-i-n Organic Photovoltaic Devices Using Tetrabenzoporphyrin Precursor and Silylmethyl[60]fullerene. *J. Am. Chem. Soc.* 2009, 131, (44), 16048-16050.
8. Illescas, B. M.; Martin, N., [60]Fullerene-based electron acceptors. *Comptes Rendus Chimie* 2006, 9, (7-8), 1038-1050.
9. Kooistra, F. B.; Knol, J.; Kastenberg, F.; Popescu, L. M.; Verhees, W. J. H.; Kroon, J. M.; Hummelen, J. C., Increasing the Open Circuit Voltage of Bulk-Heterojunction Solar Cells by Raising the LUMO Level of the Acceptor. *Org. Lett.* 2007, 9, (4), 551-554.
10. Brabec, C. J.; Cravino, A.; Meissner, D.; Sariciftci, N. S.; Fromherz, T.; Rispens, M. T.; Sanchez, L.; Hummelen, J. C., Origin of the Open Circuit Voltage of Plastic Solar Cells. *Adv. Funct. Mater.* 2001, 11, (5), 374-380.

The invention claimed is:

1. A photovoltaic cell comprising a 1,4 fullerene derivative having the formula:

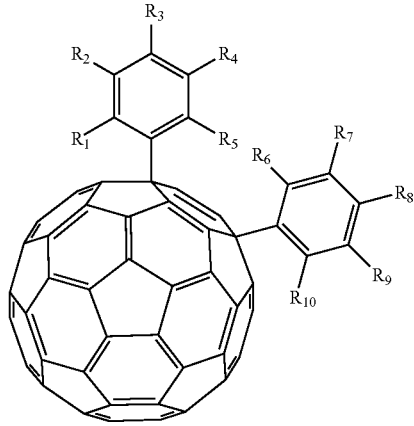

wherein:
the fullerene comprises at least 60 carbon atoms;
at least one of R1-R10 is hydrogen; and
at least one of R1-R10 is independently selected from alkyl, aryl, amino, oxo, thio, alkyl, halogen, and silanes;
wherein the derivative is selected from the group consisting of PEHOB, PCVM, PTHOB, and PFTFP.

2. A method of producing a photo voltaic cell device comprising forming a layer of the device with a compound comprising a 1,4 fullerene derivative of claim 1.

3. The photovoltaic cell of claim 1, wherein the 1,4 fullerene derivative exhibits a lowest unoccupied molecular orbital (LUMO) energy that is lower than the LUMO energy of PCBM.

4. The photovoltaic cell of claim 3, wherein the lowest unoccupied molecular orbital (LUMO) energy of the 1,4 fullerene derivative is at least 200 mV lower than the LUMO energy of PCBM.

5. The photovoltaic cell of claim 3, wherein the 1,4 fullerene derivative exhibits a lowest unoccupied molecular orbital (LUMO) energy of at least −3.76 eV as measured by cyclic voltammetry.

6. The photovoltaic cell of claim 3, wherein the 1,4 fullerene derivative exhibits a lowest unoccupied molecular orbital (LUMO) energy of at least −3.81 eV as measured by cyclic voltammetry.

7. The photovoltaic cell of claim 3, wherein the 1,4 fullerene derivative exhibits a lowest unoccupied molecular orbital (LUMO) energy of at least −3.86 eV as measured by cyclic voltammetry.

8. The photovoltaic cell of claim 3, wherein the 1,4 fullerene derivative exhibits a lowest unoccupied molecular orbital (LUMO) energy of at least −3.91 eV as measured by cyclic voltammetry.

9. The photovoltaic cell of claim 1, wherein the 1,4 fullerene derivative exhibits a lowest unoccupied molecular orbital (LUMO) energy that is higher than the LUMO energy of PCBM.

10. The photovoltaic cell of claim 9, wherein the lowest unoccupied molecular orbital (LUMO) energy of the 1,4 fullerene derivative is at least 100 mV higher than the LUMO energy of PCBM.

11. The photovoltaic cell of claim 9, wherein the 1,4 fullerene derivative exhibits a lowest unoccupied molecular orbital (LUMO) energy not greater than −3.65 eV as measured by cyclic voltammetry.

12. The method claim 2, wherein the 1,4 fullerene derivative is selected to exhibit a lowest unoccupied molecular orbital (LUMO) energy that is lower than the LUMO energy of PCBM.

13. The method claim 12, wherein the lowest unoccupied molecular orbital (LUMO) energy of the 1,4 fullerene derivative is selected to be at least 200 mV lower than the LUMO energy of PCBM.

14. The method claim 12, wherein the 1,4 fullerene derivative is selected to exhibit a lowest unoccupied molecular orbital (LUMO) energy of at least −3.76 eV as measured by cyclic voltammetry.

15. The method claim 12, wherein the 1,4 fullerene derivative is selected to exhibit a lowest unoccupied molecular orbital (LUMO) energy of at least −3.81 eV as measured by cyclic voltammetry.

16. The method claim 12, wherein the 1,4 fullerene derivative is selected to exhibit a lowest unoccupied molecular orbital (LUMO) energy of at least −3.86 eV as measured by cyclic voltammetry.

17. The method claim 12, wherein the 1,4 fullerene derivative is selected to exhibit a lowest unoccupied molecular orbital (LUMO) energy of at least −3.91 eV as measured by cyclic voltammetry.

18. The method claim 1, wherein the 1,4 fullerene derivative is selected to exhibit a lowest unoccupied molecular orbital (LUMO) energy that is higher than the LUMO energy of PCBM.

19. The method claim 18, wherein the lowest unoccupied molecular orbital (LUMO) energy of the 1,4 fullerene derivative is at least 100 mV higher than the LUMO energy of PCBM.

\* \* \* \* \*